US010345268B2

(12) United States Patent
Kawasaki et al.

(10) Patent No.: US 10,345,268 B2
(45) Date of Patent: Jul. 9, 2019

(54) ULTRASONIC INSPECTION DEVICE AND METHOD

(71) Applicant: IHI Inspection and Instrumentation Co., Ltd., Tokyo (JP)

(72) Inventors: Hiraku Kawasaki, Kanagawa (JP); Tatsuya Hikichi, Kanagawa (JP); Saburou Shibata, Kanagawa (JP); Hideyuki Nakamura, Kanagawa (JP); Takahiro Arakawa, Kanagawa (JP)

(73) Assignee: IHI Inspection and Instrumentation Co., Ltd., Tokyo (JP)

( * ) Notice: Subject to any disclaimer, the term of this patent is extended or adjusted under 35 U.S.C. 154(b) by 275 days.

(21) Appl. No.: 14/625,788

(22) Filed: Feb. 19, 2015

(65) Prior Publication Data

US 2015/0160167 A1 Jun. 11, 2015

Related U.S. Application Data

(63) Continuation of application No. PCT/JP2013/074016, filed on Sep. 6, 2013.

(30) Foreign Application Priority Data

Sep. 10, 2012 (JP) ................................. 2012-198376

(51) Int. Cl.
*G01N 29/06* (2006.01)
*G01N 29/07* (2006.01)
*G01N 29/34* (2006.01)

(52) U.S. Cl.
CPC ........... *G01N 29/07* (2013.01); *G01N 29/069* (2013.01); *G01N 29/348* (2013.01);
(Continued)

(58) Field of Classification Search
CPC ......... G01N 2291/0234; G01N 29/069; G01N 29/07; G01N 29/348; G01N 229/011; G01N 2291/044; G01N 2291/102
See application file for complete search history.

(56) References Cited

U.S. PATENT DOCUMENTS 5,895,855 A 4/1999 Ishikawa et al.
6,644,119 B1 11/2003 Sinha
(Continued)

FOREIGN PATENT DOCUMENTS

JP 8-122308 A 5/1996
JP 9-281093 A 10/1997
(Continued)

OTHER PUBLICATIONS

Kawasai, Hiraku et al, "Resolution Improvement of Underground Images Using Pulse Compression," Japanese Journal of Applied Physics 48 (2009) 07GC08.
(Continued)

*Primary Examiner* — Justin Seo
*Assistant Examiner* — John M Royston
(74) *Attorney, Agent, or Firm* — Griffin and Szipl PC

(57) ABSTRACT

An ultrasonic transmitter 3 attached to an inspecting target object 1, an ultrasonic receiver 5 receiving a reflected wave of the ultrasonic wave that has propagated from the ultrasonic transmitter 3 in the inspecting target object, a data processing device 7 acquiring position specifying data for specifying a position of a defect 1a in the inspecting target object 1 on the basis of received data representing a waveform of the reflected wave received by the ultrasonic receiver 5 are provided. The ultrasonic wave generated by the ultrasonic transmitter 3 has been frequency-modulated, and has a waveform composed of components of respective frequencies that are deviated from a resonance frequency of (Continued)

the ultrasonic transmitter 3 and the ultrasonic receiver 5. The data processing device 7 includes a pulse compressing unit 21 performing pulse compression on the received data, and acquires the position specifying data on the basis of the pulse-compressed received data.

5 Claims, 11 Drawing Sheets

(52) U.S. Cl.
CPC ............. *G01N 2291/011* (2013.01); *G01N 2291/0234* (2013.01); *G01N 2291/044* (2013.01); *G01N 2291/102* (2013.01)

(56) References Cited

U.S. PATENT DOCUMENTS

| | | | |
|---|---|---|---|
| 6,959,601 B2 | 11/2005 | Sinha | |
| 2002/0151798 A1* | 10/2002 | Honda | A61B 8/481 600/458 |
| 2004/0035190 A1 | 2/2004 | Sinha | |
| 2004/0211240 A1* | 10/2004 | Gessert | G01N 29/2487 73/1.82 |
| 2005/0097943 A1 | 5/2005 | Sinha | |
| 2009/0007678 A1* | 1/2009 | Fukutomi | G01N 29/069 73/598 |
| 2010/0251822 A1* | 10/2010 | Isobe | G01N 29/069 73/606 |
| 2011/0120209 A1* | 5/2011 | Rose | G01H 11/08 73/1.82 |

FOREIGN PATENT DOCUMENTS

| | | |
|---|---|---|
| JP | 11-094808 A | 4/1999 |
| JP | 2004-117137 A | 4/2004 |
| JP | 2005-265747 A | 9/2005 |
| JP | 2005-531768 A | 10/2005 |
| JP | 2008-521547 A | 6/2008 |
| JP | 2008-151599 A | 7/2008 |
| JP | 2012-042449 A | 3/2012 |
| WO | 2006/059966 A1 | 6/2006 |

OTHER PUBLICATIONS

International Search Report issued in corresponding application No. PCT/JP2013/074016, completed Nov. 14, 2013 and dated Nov. 26, 2013.
European Search Report issued in corresponding application 13835241.4 completed Aug. 24, 2015 and dated Sep. 11, 2015.

* cited by examiner

[Fig 1]
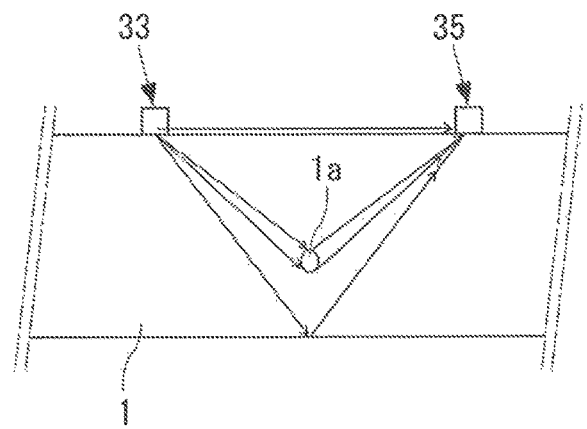
[Fig 2]
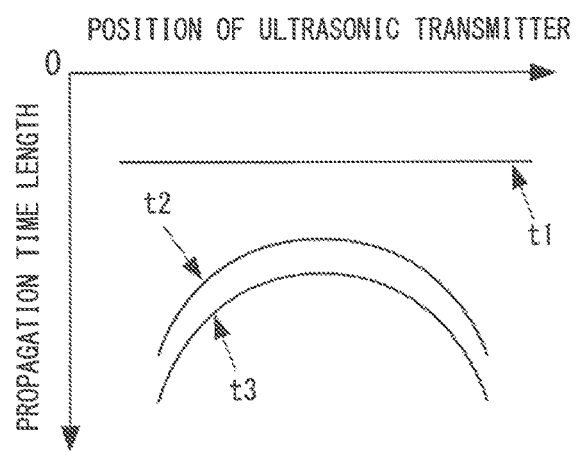

[Fig 3]
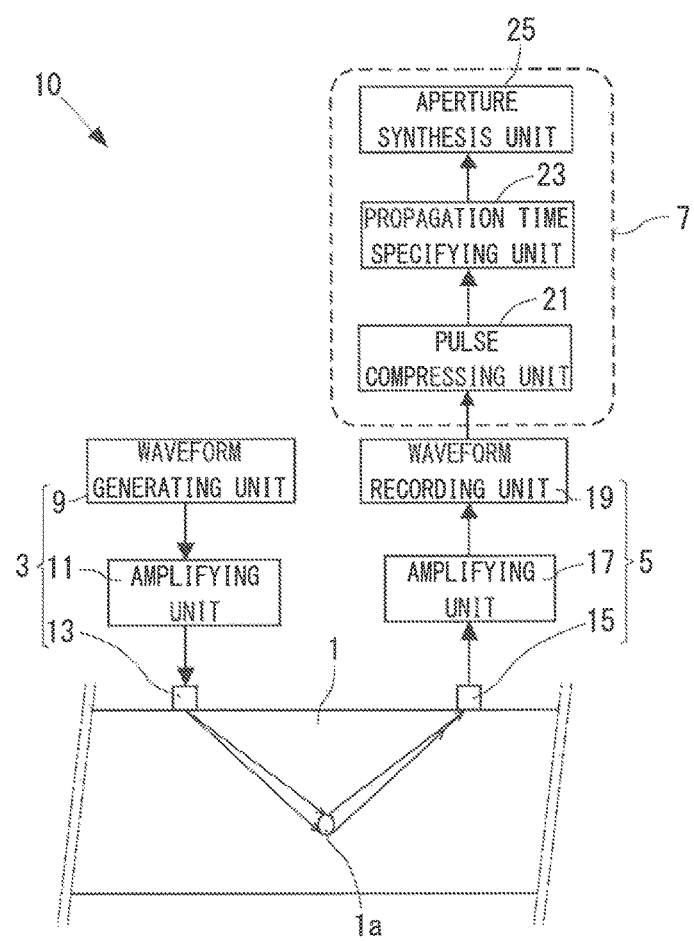

[Fig 4]
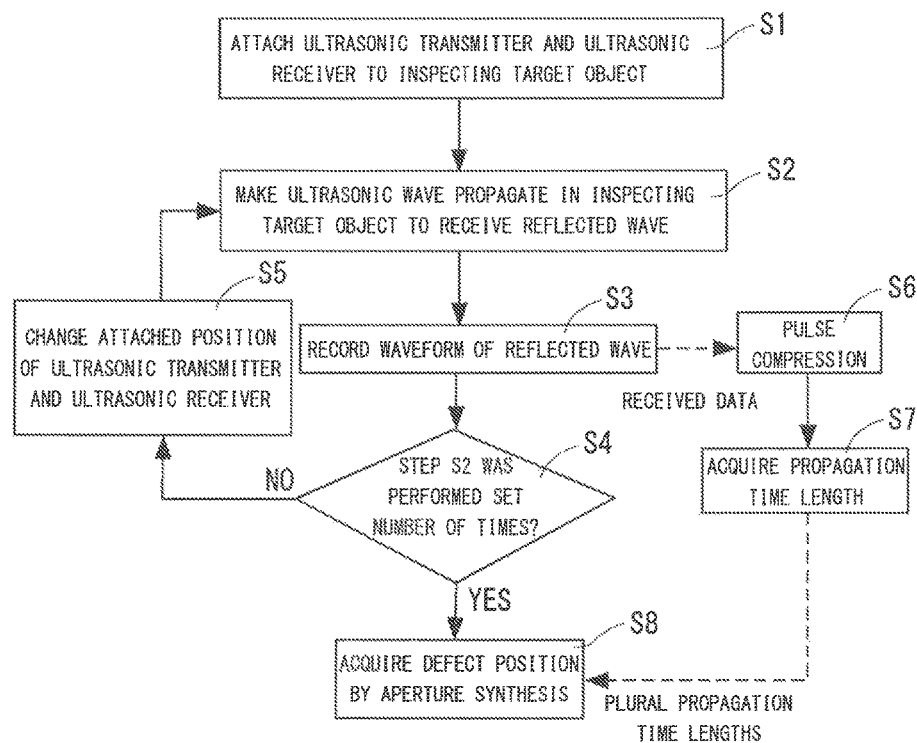

[Fig 5]
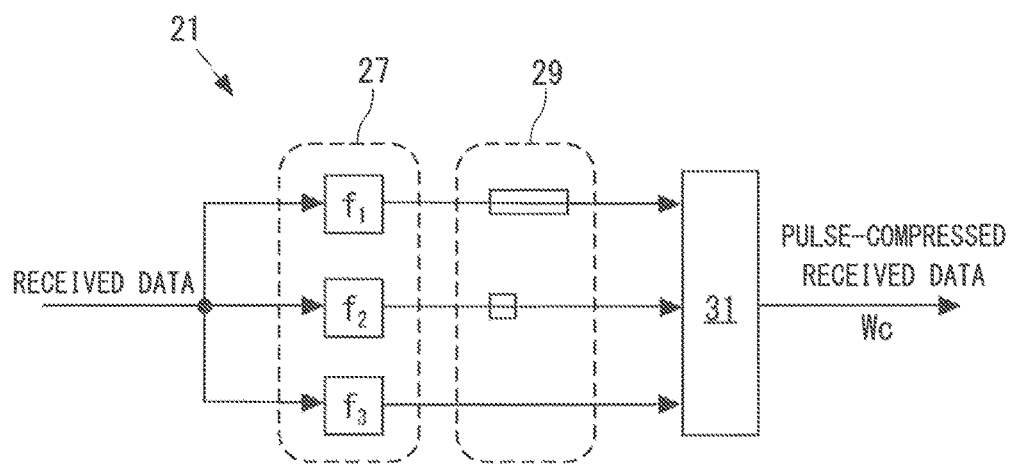

[Fig 6]
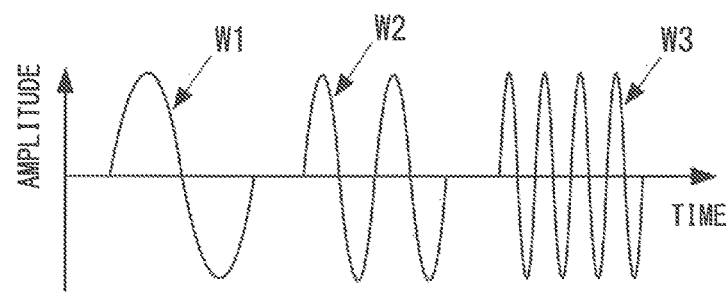

[Fig 7]
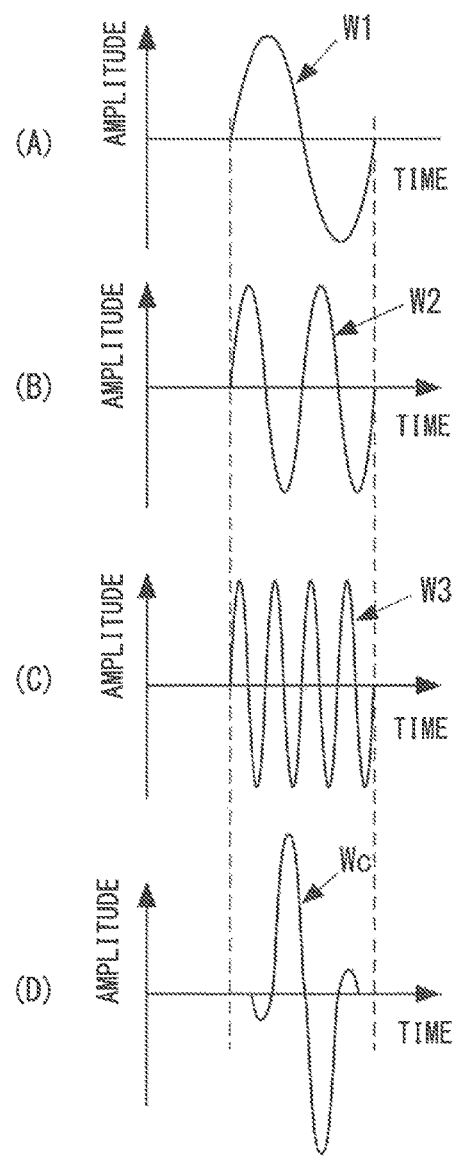

[Fig 8]
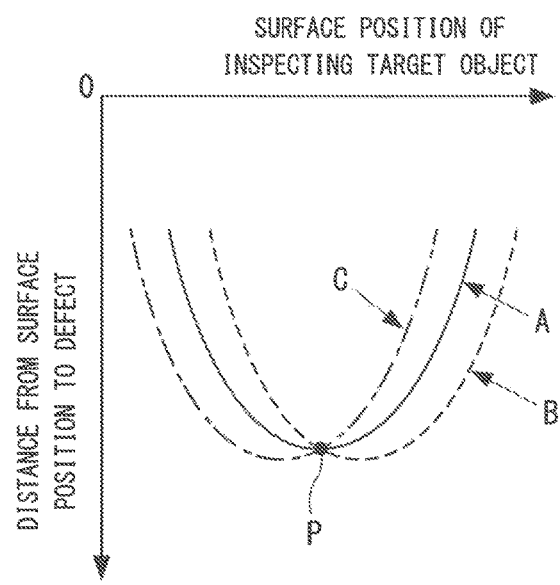

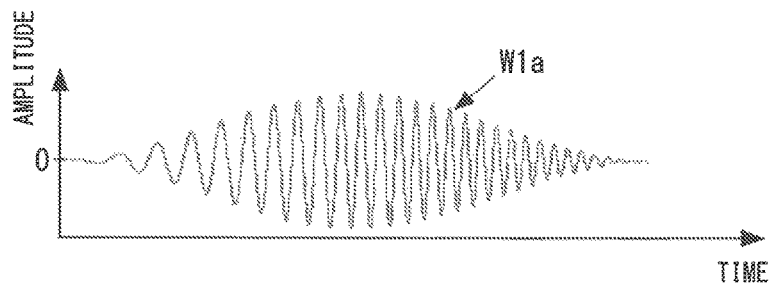
[Fig 9A]
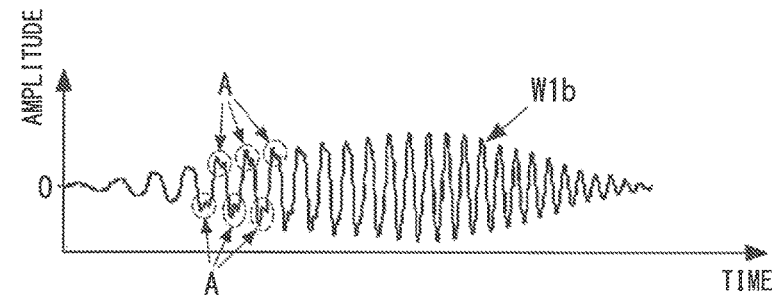
[Fig 9B]
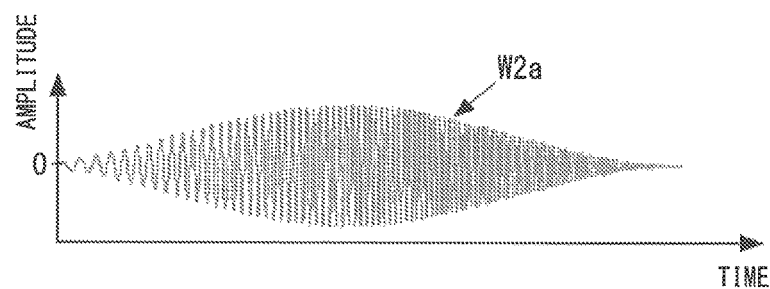
[Fig 9C]
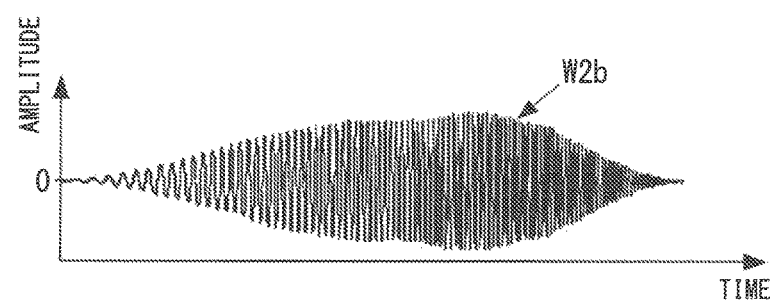
[Fig 9D]

[Fig 10]
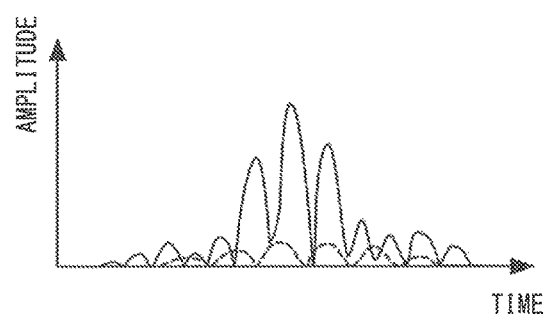

[Fig 11A]
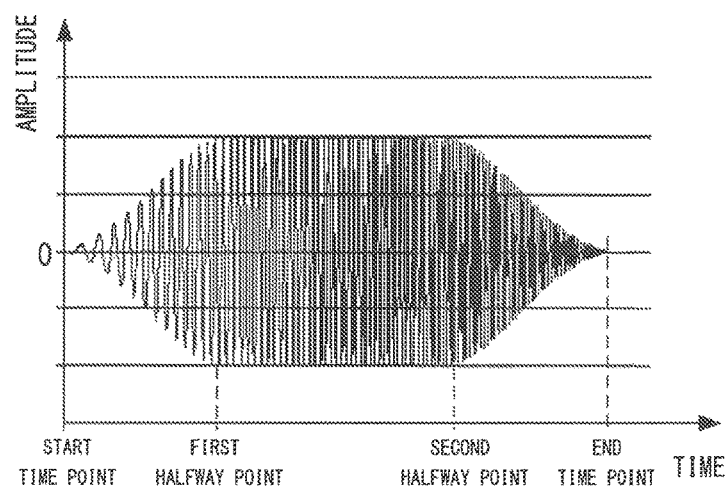
[Fig 11B]
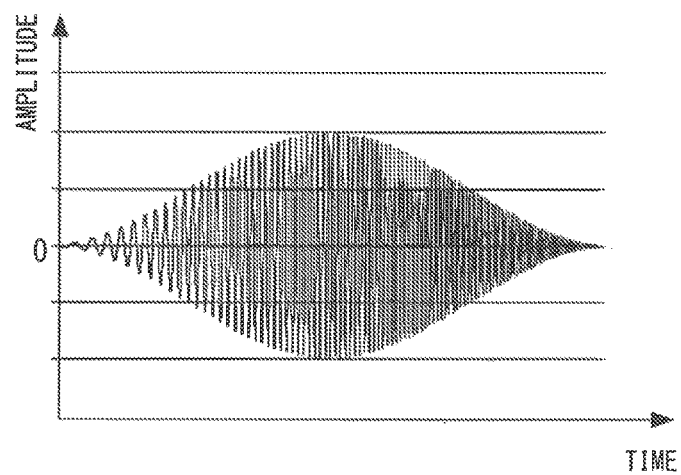

[Fig 12A]
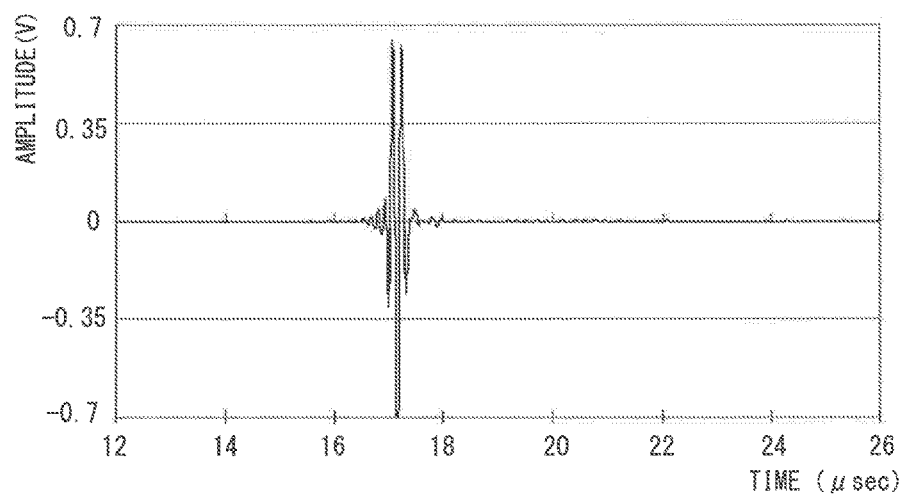
[Fig 12B]
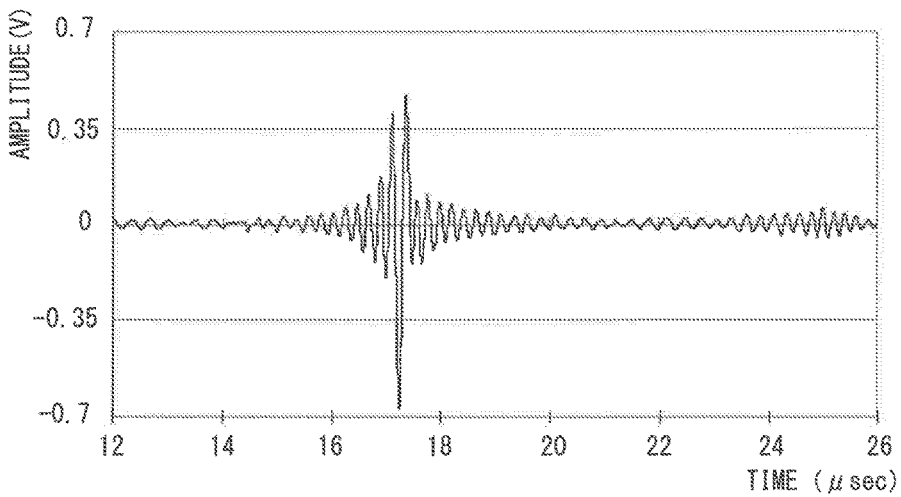

ULTRASONIC INSPECTION DEVICE AND METHOD

This is a Continuation Application in the United States of International Patent Application No. PCT/JP2013/074016 filed Sep. 6, 2013, which claims priority on Japanese Patent Application No. 2012/198376, filed Sep. 10, 2012. The entire disclosures of the above patent applications are hereby incorporated by reference.

TECHNICAL FIELD

The present invention relates to an ultrasonic inspection device and method for making an ultrasonic wave propagate in an inspecting target object, and acquiring a position of a defect in the inspecting target object on the basis of the ultrasonic wave reflected by the defect in the inspecting target object.

BACKGROUND ART

For example, an inspecting target object is a metal member (steel member) including a welded part, and a position of a defect in the welded part of the inspecting target object is acquired by an ultrasonic wave.

As this inspection method, there is a time-of-flight diffraction (TOFD) method.

This TOFD method is performed as follows. In FIG. 1, an ultrasonic transmitter 33 generates an ultrasonic wave. This ultrasonic wave includes a lateral wave propagating on a surface of an inspecting target object 1, and an inside-propagation wave propagating inside the inspecting target object 1. The inside-propagation wave includes a wave reflected by an upper end of a defect 1a (defect in a welded part in this example) inside the inspecting target object 1, a wave reflected by a lower end of the defect 1a, and a wave reflected by a bottom of the inspecting target object 1. A timing of generating the ultrasonic wave is set as an origin for time measurement. The time that an ultrasonic receiver 35 detects the lateral wave is set as t1. The time that the ultrasonic receiver 35 detects the reflection wave from the upper end of the defect 1a is set as t2. The time that the ultrasonic receiver 35 detects the reflection wave from the lower end of the defect 1a is set as t3. The time that the ultrasonic receiver 35 detects the reflection wave from the bottom of the inspecting target object 1 is set as t4. While a distance between the ultrasonic transmitter 33 and the ultrasonic receiver 35 is kept constant, an attached position of the ultrasonic transmitter 33 and the ultrasonic receiver 35 to the inspecting target object 1 is gradually moved to the right side in FIG. 1, and at each attached position, the above-mentioned time t1 to t4 is detected by the ultrasonic transmitter 33 and the ultrasonic receiver 35.

The thus-acquired time data is illustrated in FIG. 2 (illustration of t4 is omitted). In FIG. 2, the horizontal axis indicates a position of the ultrasonic transmitter 33, and the vertical axis indicates time in which the timing of generating the ultrasonic wave is the origin. The time t1 to t3 is expressed by the straight line or the curved lines illustrated in FIG. 2. It can be assumed that when the time t2 and the time t3 becomes minimum, a distance from the ultrasonic transmitter 33 to the defect 1a is equal to a distance from the ultrasonic receiver 35 to the defect 1a. Accordingly, on the basis of the minimum values of t2 and t3, and a known distance between the ultrasonic transmitter 33 and the ultrasonic receiver 35, a position (a location in the left-to-right direction and a distance from this location to the defect 1a in FIG. 1) of the defect 1a can be acquired.

Such a TOFD method is described in below-mentioned Patent Literature (PTL) 1, for example. Concerning amplitude modulation in an embodiment of the present invention, there is below-mentioned Non-Patent Literature (NPL) 1.

CITATION LIST

Patent Literatures

PTL 1: Japanese Patent Application Laid-open No. 2004-117137

Non-Patent Literatures

NPL: Resolution Improvement of Underground Images Using Pulse Compression, Japanese Journal of Applied Physics, 48 (2009) 07GC08

SUMMARY OF INVENTION

Technical Problem

In order to specify a position of a defect in an inspecting target object with high accuracy, it is considered to use pulse compression. In this case, an ultrasonic transmitter generates a frequency-modulated ultrasonic wave, and this ultrasonic wave is received by an ultrasonic receiver to acquire received data. This received data is pulse-compressed so that the position of the defect can be specified with high accuracy.

Conventionally, in order to generate an ultrasonic wave at high efficiency, a waveform of a frequency-modulated ultrasonic wave includes a component of a resonance frequency of an ultrasonic transmitter.

However, in a frequency-modulated ultrasonic wave, a distortion often occurs. For example, FIG. 9B described later is data of a reflected wave of a frequency-modulated ultrasonic wave. In FIG. 9B, at a part surrounded by the broken line A, a distortion occurs in a waveform of the ultrasonic wave.

In view of it, an object of the present invention is to make it possible to eliminate a distortion in a frequency-modulated ultrasonic wave, thereby acquiring a defect position with higher accuracy in a case where the frequency-modulated ultrasonic wave is generated, and received data of a reflected ultrasonic wave thereof is pulse-compressed.

Solution to Problem

In order to accomplish the above-described object, the present invention is an ultrasonic inspecting device for making an ultrasonic wave propagate in an inspecting target object, and acquiring a position of a defect in the inspecting target object on the basis of the ultrasonic wave reflected by the defect in the inspecting target object, the ultrasonic inspecting device comprising:

an ultrasonic transmitter attached to the inspecting target object, and causing an ultrasonic wave propagating in the inspecting target object to be generated;

an ultrasonic receiver receiving a reflected wave of the ultrasonic wave that has propagated in the inspecting target object;

a data processing device acquiring position specifying data for specifying the position of the defect in the inspecting target object, on the basis of received data representing a waveform of the reflected wave received by the ultrasonic receiver;

wherein the ultrasonic wave generated by the ultrasonic transmitter has been frequency-modulated, and has a waveform composed of components of respective frequencies that are deviated from a resonance frequency of the ultrasonic transmitter and the ultrasonic receiver, and the data processing device includes a pulse compressing unit performing pulse compression on the received data, and acquires the position specifying data on the basis of the pulse-compressed received data.

According to a preferred embodiment of the present invention, the ultrasonic transmitter generates the ultrasonic wave that has been frequency-modulated for a set time period, and an amplitude of the ultrasonic wave gradually increases from a start time point of the set time period to a first halfway time point, is kept constant from the first halfway time point to a second halfway time point, and gradually decreases from the second halfway time point to an end time point of the set time period.

According to a preferred embodiment of the present invention, attached positions of the ultrasonic transmitter and the ultrasonic receiver to the inspecting target object are changed, or a plurality of ultrasonic transmitters and a plurality of ultrasonic receivers are installed at attached positions different from each other, at each of the attached positions, the ultrasonic transmitter makes the ultrasonic wave propagate in the inspecting target object, and the ultrasonic receiver receives the reflected wave of the ultrasonic wave, the ultrasonic inspecting device includes a waveform recording unit that records the received data acquired for each of the attached positions, and the data processing device comprises:

a propagation time specifying unit acquiring, as the position specifying data, a propagation time length from a time point when the ultrasonic transmitter generates the ultrasonic wave to a time point when the ultrasonic receiver receives the reflected wave of the ultrasonic wave, on the basis of the received data for each of the attached positions; and an aperture synthesis unit performing aperture synthesis on a plurality of propagation time lengths acquired respectively for a plurality of the attached positions to acquire the position of the defect in the inspecting target object.

Further, in order to accomplish the above-described object, the present invention is an ultrasonic inspecting method for making an ultrasonic wave propagate in an inspecting target object, and acquiring a position of a defect in the inspecting target object on the basis of the ultrasonic wave reflected by the defect in the inspecting target object, the ultrasonic inspecting method comprising:

(A) attaching an ultrasonic transmitter and an ultrasonic receiver to the inspecting target object;

(B) by the ultrasonic transmitter, generating the ultrasonic wave that propagates in the inspecting target object;

(C) by the ultrasonic receiver, receiving a reflected wave of the ultrasonic wave that has propagated in the inspecting target object by the step (B); and (D) acquiring position specifying data for specifying the position of the defect in the inspecting target object, on the basis of received data representing a waveform of the reflected wave received by the ultrasonic receiver;

wherein the ultrasonic wave generated by the step (B) has been frequency-modulated, and has a waveform composed of components of respective frequencies that are deviated from a resonance frequency of the ultrasonic transmitter and the ultrasonic receiver, and at the step (D), pulse compression is performed on the received data, and on the basis of the pulse-compressed received data, the position specifying data is acquired.

Advantageous Effects of Invention

In the above-described present invention, a frequency-modulated ultrasonic wave from the ultrasonic transmitter is composed of components of respective frequencies deviated from the resonance frequency of the ultrasonic transmitter and the ultrasonic receiver so that a distortion of a waveform of the ultrasonic wave can be prevented. This was confirmed by the experiment as described below.

BRIEF DESCRIPTION OF DRAWINGS

FIG. 1 is an illustration of an ultrasonic inspecting method by a TOFD method.

FIG. 2 is a graph indicating a propagation time length of an ultrasonic wave acquired by the TOFD method.

FIG. 3 illustrates an ultrasonic inspecting device according to an embodiment of the present invention.

FIG. 4 is a flowchart illustrating an ultrasonic inspecting method according to an embodiment of the present invention.

FIG. 5 illustrates a pulse compressing unit.

FIG. 6 illustrates waveforms of respective frequency components decomposed for pulse compression.

FIG. 7 illustrates waveforms of the frequency components of which positions on time axes are adjusted for the pulse compression by (A) to (C), and illustrates a pulse-compressed waveform by (D).

FIG. 8 is an illustration of aperture synthesis.

FIG. 9A illustrates a generated waveform of an ultrasonic wave including a component of a resonance frequency of a transmitting oscillator and a receiving oscillator.

FIG. 9B illustrates a received waveform of the ultrasonic wave including the component of the resonance frequency of the transmitting oscillator and the receiving oscillator.

FIG. 9C illustrates a generated waveform of an ultrasonic wave that does not include a resonance frequency of a transmitting oscillator.

FIG. 9D illustrates a received waveform of the ultrasonic wave that does not include the resonance frequency of the transmitting oscillator.

FIG. 10 is a graph illustrating an advantageous effect by amplitude modulation according to the embodiment of the present invention.

FIG. 11A illustrates an amplitude-modulated waveform according to the embodiment of the present invention.

FIG. 11B illustrates an amplitude-modulated waveform of a comparison example.

FIG. 12A illustrates a waveform of received data according to an embodied example of the present invention.

FIG. 12B illustrates a waveform of received data according to the comparison example.

DESCRIPTION OF EMBODIMENTS

A preferred embodiment of the present invention is described in detail below with reference to the accompanying drawings. Elements common to the respective drawings are denoted by the same reference numerals, and repeated description is omitted.

FIG. 3 illustrates an ultrasonic inspecting device 10 according to an embodiment of the present invention. The ultrasonic inspecting device 10 causes an ultrasonic wave to propagate in an inspecting target object 1, and acquires a position of a defect 1a in the inspecting target object 1 on the basis of an ultrasonic wave reflected by the defect 1a in the inspecting target object 1. The inspecting target object 1 is a metal member (e.g., steel member). In this case, the defect 1a (e.g., void) exists in a welded part of the metal member. However, according to the present invention, the inspecting target object 1 and the defect 1a may be others.

The ultrasonic inspecting device 10 includes an ultrasonic transmitter 3, an ultrasonic receiver 5, and a data processing device 7.

The ultrasonic transmitter 3 is attached to the inspecting target object 1, and generates an ultrasonic wave that propagates in the inspecting target object 1. The ultrasonic wave generated by the ultrasonic transmitter 3 has been frequency-modulated, and the waveform of this ultrasonic wave is formed by components of respective frequencies that deviate from a resonance frequency of the ultrasonic transmitter 3 and the ultrasonic receiver 5. The ultrasonic transmitter 3 includes a waveform generating unit 9, an amplifying unit 11, and a transmitting oscillator 13.

The waveform generating unit 9 generates a voltage of a waveform that has been frequency-modulated as described above, and been amplitude-modulated. By the frequency modulation, a frequency of this waveform gradually increases or decreases over a set time period as time elapses. By the amplitude modulation, an amplitude of this waveform gradually increases from s start time point to a first halfway time point in the set time period, is then kept constant from the first halfway time point to a second halfway point, and gradually decreases from the second halfway time point to an end time point of the set time period (a concrete example of this waveform is described below with reference to the FIG. 11A). Preferably, time from the first halfway point to the second halfway point in the set time period is equal to or longer than one third of time from the start time point to the end time point of the set time period.

The thus-amplitude-modulated waveform can suppress attenuation of an ultrasonic wave when the ultrasonic wave is propagating in the inspecting target object 1. In other words, even when an ultrasonic wave from the ultrasonic transmitter 3 (transmitting oscillator 13) passes through a part that tends to cause attenuation, or propagates over a long distance, attenuation thereof can be suppressed to be small. The part that tends to cause attenuation is a welded part in the metal inspecting target object 1, a boundary between parts of different materials in the inspecting target object 1, or a part formed of a low-density material (e.g., stainless steel).

The above-described amplitude modulation is preferably performed by using a window function expressed by the following formula 1. In the formula 1, k is an arbitrary value, t indicates time, and $P_{tr}$ indicates a pre-trigger rate. By the formula 1, a waveform having an amplitude expressed by W(t) is generated.

$$f(x) = \int_0^x x^k(1-x)^k dx \quad \text{[Formula 1]}$$

-continued $$W(t) = \begin{cases} \dfrac{f(P_{tr}-t)}{\int_0^1 x^k(1-x)^k dx} & 0 \leq t \leq P_{tr} \\ 1 & P_{tr} \leq t \leq 1-P_{tr} \\ \dfrac{f(P_{tr}(0.1-t))}{\int_0^1 x^k(1-x)^k dx} & 1-P_{tr} \leq t \leq 1 \end{cases}$$

The waveform generated by the waveform generating unit 9 does not include a component of the resonance frequency of the ultrasonic transmitter 3 (transmitting oscillator 13) and the ultrasonic receiver 5 (receiving oscillator 15). In other words, the waveform generated by the waveform generating unit 9 is formed by components of respective frequencies that deviate from the resonance frequency of the ultrasonic transmitter 3 (transmitting oscillator 13) and the ultrasonic receiver 5 (receiving oscillator 15). Thereby, a distortion of an ultrasonic wave generated by the ultrasonic transmitter 3 can be prevented.

The amplifying unit 11 amplifies, at a fixed gain, a voltage of the waveform generated by the waveform generating unit 9, and then applies the voltage to the transmitting oscillator 13.

The transmitting oscillator 13 is attached to the inspecting target object 1. In a state where the transmitting oscillator 13 is attached to the inspecting target object 1, a voltage having the waveform generated by the waveform generating unit 9 is applied to the transmitting oscillator 13. Thereby, the transmitting oscillator 13 oscillates to generate an ultrasonic wave in the inspecting target object 1. This ultrasonic wave has the waveform (i.e., time change in a frequency and an amplitude) conforming to the waveform generated by the waveform generating unit 9. Such a transmitting oscillator 13 may be a piezoelectric element.

The ultrasonic receiver 5 receives a reflected wave of the ultrasonic wave that has propagated in the inspecting target object 1, and records received data representing a waveform of the reflected wave. The ultrasonic receiver 5 includes a receiving oscillator 15, an amplifying unit 17, and a waveform recording unit 19.

The receiving oscillator 15 oscillates by receiving a reflected wave of the ultrasonic wave that has propagated in the inspecting target object 1, and generates a voltage of a waveform depending on this oscillation. Such a receiving oscillator 15 may be a piezoelectric element.

The amplifying unit 17 amplifies, at the fixed gain, a voltage generated by the receiving oscillator 15.

The waveform recording unit 19 records received data representing a waveform of a voltage amplified by the amplifying unit 17.

The data processing unit 7 includes a pulse compressing unit 21, a propagation time specifying unit 23, and an aperture synthesis unit 25.

The pulse compressing unit 21 performs pulse compression on received data recorded by the waveform recording unit 19. On the basis of the pulse-compressed received data, the data processing unit 7 acquires position specifying data for specifying a position of the defect 1a in the inspecting target object 1.

The propagation time specifying unit 23 acquires, as the above-mentioned position specifying data, a propagation time length from a time point that the transmitting oscillator 13 generates an ultrasonic wave to a time point that the receiving oscillator 15 receives a reflected wave of this ultrasonic wave, on the basis of the waveform pulse-compressed by the pulse compressing unit 21.

For each attached position of the transmitting oscillator 13 and the receiving oscillator 15, the propagation time length is specified by the receiving oscillator 15, the amplifying unit 17, the pulse compressing unit 21, and the propagation time specifying unit 23. Specifically, it is assumed that positions of the transmitting oscillator 13 and the receiving oscillator 15 are the same as each other in the direction perpendicular to the paper sheet surface of FIG. 3, positions of the transmitting oscillator 13 and the receiving oscillator 15 attached to the inspecting target object 1 are gradually moved in the left-to-right direction of FIG. 3 while a distance between the transmitting oscillator 13 and the receiving oscillator 15 are kept constant. At each of the attached positions of the transmitting oscillator 13 and the receiving oscillator 15, an ultrasonic wave is generated from the transmitting oscillator 13, a reflected wave of this ultrasonic wave is received by the receiving oscillator 15, and on the basis of received data representing this reflected wave, the propagation time length is specified by the amplifying unit 17, the pulse compressing unit 21, and the propagation time specifying unit 23. In other words, for each of the attached positions, the propagation time length from the time point that the ultrasonic transmitter 3 generates the ultrasonic wave to the time point that the ultrasonic receiver 5 receives the reflected wave of this ultrasonic wave is acquired by the amplifying unit 17, the pulse compressing unit 21, and the propagation time specifying unit 23 on the basis of the received data representing the waveform of the reflected wave received by the receiving oscillator 15.

In the present patent application, the attached position of the ultrasonic transmitter 3 (transmitting oscillator 13) and the ultrasonic receiver 5 (receiving oscillator 15) means a position of the ultrasonic transmitter 3 or the ultrasonic receiver 5.

The aperture synthesis unit 25 performs aperture synthesis on a plurality of the propagation time lengths acquired for a plurality of the attachment positions, respectively. Thereby, the aperture synthesis unit 25 acquires a position of the defect 1a in the inspecting target object 1.

FIG. 4 is a flowchart illustrating an ultrasonic inspecting method according to an embodiment of the present invention.

At the step S1, the ultrasonic transmitter 3 and the ultrasonic receiver 5 are attached to the inspecting target object 1.

At the step S2, an ultrasonic wave that propagates in the inspecting target object 1 is generated by the ultrasonic transmitter 3, and a reflected wave of this ultrasonic wave that has propagated in the inspecting target object 1 is received by the ultrasonic receiver 5.

At the step S3, received data representing a waveform of the reflected wave received by the ultrasonic receiver 5 is recorded by the waveform recording unit 19.

At the step S4, it is determined whether or not the step S2 has been performed the set number of times. When the determination result is negative, the process advances to the step S5, and the determination result is affirmative, the process advances to the step S8. The set number of times is an integer equal to or larger than two.

At the step S5, while a distance between the transmitting oscillator 13 and the receiving oscillator 15 is kept constant, positions of the transmitting oscillator 13 and the receiving oscillator 15 attached to the inspecting target object 1 are changed. In an example of FIG. 3, the attached position is changed in the left-to-right direction in FIG. 3.

When the step S5 is finished, the process returns to the step S2, and the steps S2 and S3 are then performed again.

For each received data acquired by the steps S2 and S3, the steps S6 and S7 are performed on the received data.

At the step S6, by the pulse compression unit 21, the pulse compression is performed on the received data recorded at the step S3.

At the step S7, by the propagation time specifying unit 23, a propagation time length from a time point that the transmitting oscillator 13 generated an ultrasonic wave to a time point that the ultrasonic receiver 15 received the reflected wave of this ultrasonic wave is acquired on the basis of a waveform pulse-compressed by the step S6.

At the step S8, by the aperture synthesis unit 25, the aperture synthesis is performed on a plurality of the propagation time lengths respectively acquired at the step S7 for the attached positions whose number is the same as the set number of times. Thereby, a position of the defect 1a in the inspecting target object 1 is acquired.

The pulse compression at the step S6 is described in detail.

As illustrated in FIG. 5, the pulse compressing unit 21 includes a decomposing unit 27, a time axis adjusting unit 29, and an adding unit 31. The decomposing unit 27 decomposes the input received data into a plurality of frequency components different from each other. In an example of FIG. 5, the decomposing unit 27 decomposes the received data into waveforms of three frequency components W1, W2, and W3 having frequencies f1, f2, and f3, respectively. The waveforms of the frequency components W1, W2, and W3 are illustrated in FIG. 6. The time axis adjusting unit 29 makes reference time points (e.g., the start time point or the end time point of the waveforms) of the waveforms of a plurality of the decomposed frequency components (W1, W2, and W3 in the example of FIG. 6) match with each other in a time axis. The waveforms of the frequency components W1, W2, and W3 of which reference time points have been made to match with each other are illustrated in (A), (B), and (C) in FIG. 7. The adding unit 31 superimposes, on each other, the waveforms of a plurality of the frequency components of which reference time points have been made to match with each other. In other words, for each time point, the adding unit 31 adds together displacements (values in the vertical axes in FIG. 7) of the waveforms of a plurality of the frequency components. Thereby, the received data that has been pulse-compressed is output from the adding unit 31. In an example of FIG. 5, the adding unit 31 superimposes the waveforms of the frequency components W1, W2, and W3 to output the pulse-compressed received data Wc illustrated in FIG. 7(D).

The aperture synthesis at the step S8 is described in detail.

On the basis of the propagation time length, the aperture synthesis unit 25 generates the position specifying data concerning each attached position of the transmitting oscillator 13 and the receiving oscillator 15. The position specifying data indicates a range in which the defect 1a can exist. In other words, the position specifying data indicates relation between a position on the surface of the inspecting target object 1 and a distance from this position on the surface to the defect 1a.

FIG. 8 illustrates the position specifying data A, B, and C. In FIG. 8, the horizontal axis indicates a position on the surface of the inspecting target object 1, and corresponds to a position in the left-to-right direction of FIG. 3. In FIG. 8, the vertical axis indicates a distance from the position on the surface of the inspecting target object 1 to the defect 1a. In FIG. 8, the position specifying data A depicted by the solid line, the position specifying data B depicted by the broken line, and the position specifying data C depicted by the one-dot chain line is generated respectively for attached positions different from each other.

The aperture synthesis unit 25 specifies a position of the defect 1a in the inspecting target object 1 on the basis of plural sets of the position specifying data generated as described above. A position of the defect 1a means a position (a coordinate in the horizontal axis of FIG. 8) on the surface of the inspecting target object 1, and a distance (a coordinate in the vertical axis of FIG. 8) from this position on the surface to the defect 1a. With reference to FIG. 8, the aperture synthesis unit 25 specifies, as a position of the defect 1a, an intersection point P of the three curved line depicted by the position specifying data A, B, and C.

According to the above-described embodiment, the following advantageous effects can be obtained.

In the above-described embodiment, an ultrasonic wave generated by the ultrasonic transmitter 3 does not include a component of the resonance frequency of the ultrasonic transmitter 3. For this reason, a distortion of the oscillated ultrasonic wave can be prevented.

Meanwhile, differently from the present invention, in a case where a frequency-modulated ultrasonic wave from the ultrasonic transmitter 3 includes a component of the resonance frequency of the ultrasonic transmitter 3 and the ultrasonic wave receiver 5, when free resonance occurs in the ultrasonic transmitter 3 or the ultrasonic wave receiver 5, additional vibration occurs only at the component of the resonance frequency. In this case, in the prior art, by frequency modulation of a chirp wave, the wave number only for the resonance frequency is increased so that a component of the resonance frequency and component of another frequency overlap each other. For this reason, a waveform distortion is generated. On the other hand, in the embodiment of the present invention, such a distortion can be prevented.

This advantageous effect is described on the basis of FIG. 9A to FIG. 9D. FIG. 9A and FIG. 9B respectively illustrate a waveform W1a generated by the waveform generating unit 9 in a comparison example, and a waveform W1b of received data corresponding to the waveform W1a. The waveform W1a includes a component of the resonance frequency of the transmitting oscillator 13 and the receiving oscillator 15. On the other hand, FIG. 9C and FIG. 9D illustrate a waveform W2a generated by the waveform generating unit 9 in an embodied example of the present invention, and a waveform W2b of received data corresponding to the waveform W2a. The waveform W2a does not include a component of the resonance frequency of the transmitting oscillator 13 and the receiving oscillator 15.

Description is made about the case of FIG. 9A and FIG. 9B. The transmitting oscillator 13 and the receiving oscillator 15 have the resonance frequency of 5 MHz. In FIG. 9A and FIG. 9B, the waveform generating unit 9 generated the waveform W1a including components of successive frequencies from 1 MHz to 10 MHz that include the resonance frequency of 5 MHz. As illustrated in FIG. 9B, the waveform W1b of the received data corresponding to the waveform W1a was distorted at a part surrounded by the broken line A.

On the contrary, in the case of FIG. 9C and FIG. 9D, the following result was obtained. The transmitting oscillator 13 and the receiving oscillator 15 have the resonance frequency of 15 MHz. In FIG. 9C, the waveform generating unit 9 generated the waveform W2a including components of successive frequencies from 1 MHz to 10 MHz that do not include the resonance frequency of 15 MHz. As illustrated in FIG. 9D, the waveform W2b of the received data corresponding to the waveform W2a was not distorted.

An amplitude of an ultrasonic wave generated by the transmitting oscillator 13 gradually increases from the start time point of the set time period to the first halfway time point, is then kept constant from the first halfway time point to the second halfway time point, and gradually decreases from the second halfway time point to the end time point of the set time period. Thereby, attenuation of an ultrasonic wave propagating in the inspecting target object 1 can be suppressed.

This advantageous effect is described on the basis of FIG. 10. FIG. 10 illustrates a waveform in an embodied example in a case where a propagation time length was 50 microseconds. In FIG. 10, the solid line indicates magnitude of an amplitude of received data when the waveform generating unit 9 generated a waveform of FIG. 11A, and the broken line indicates received data when the waveform generating unit 9 generated a waveform of FIG. 11B. As understood from FIG. 10, an ultrasonic wave of the waveform in which an amplitude was kept constant from the first halfway time point to the second halfway time point as illustrated in FIG. 11A was generated so that time for holding an amplitude of the waveform at a large value was made long. Accordingly, transmission energy particularly in a lower-frequency region was increased. As a result, components of lower frequencies remained in an ultrasonic wave after propagation in the inspecting target object 1 to decrease attenuation in the ultrasonic wave. As a result, as in the actual waveform of the solid line in FIG. 10, attenuation in the ultrasonic wave can be largely suppressed. The solid line and the broken line of FIG. 10 are data acquired in the same condition except that the waveforms of the generated ultrasonic waves are different.

EMBODIED EXAMPLE

FIG. 12A indicates a waveform of received data acquired by an embodied example of the present invention. FIG. 12B indicates a waveform of received data acquired by a comparison example.

In a case of FIG. 12A, the resonance frequency of the ultrasonic transmitter 3 and the ultrasonic receiver 5 was 15 MHz, and the ultrasonic transmitter 3 generated an ultrasonic wave including components of successive frequencies from 1 MHz to 10 MHz that do not include the resonance frequency.

In a case of FIG. 12B, the resonance frequency of the ultrasonic transmitter and the ultrasonic receiver is 5 MHz, and the ultrasonic transmitter generated an ultrasonic wave including components of successive frequencies from 1 MHz to 10 MHz that include the resonance frequency.

As understood from FIG. 12A and FIG. 12B, in the present embodied example, a length of a wave is much shorter than in the comparison example. Further, in the present embodied example, an amplitude of the waveform becomes a value close to zero at time deviated from the time points where the amplitude becomes peaks in the waveform of the received data. Meanwhile, in the comparison example, an amplitude of the waveform becomes a relatively large value even at time deviated from the time points where the amplitude becomes peaks in the waveform of the received data. In other words, in the comparison example, a side lobe is generated.

Thus, by the present embodied example, it becomes possible to specify a position of the defect 1a with more accuracy than in the prior art.

The present invention is not limited to the above-described embodiment. Of course, various modifications can be made without departing from the gist of the present invention. For example, any one of the below-described modified examples 1 to 4 may be adopted, or arbitrary combination of the modified examples 1 to 4 may be adopted. In this case, the points that are not described below may be the same as those described above.

Modified Example 1

The data processing device 7 does not need to include the aperture synthesis unit 25. In this case, at the above-described step S8, by a different method (e.g., a TOFD method), the data processing device 7 may acquire a position of the defect 1*a* in the inspecting target body 1 on the basis of propagation time lengths acquired respectively for a plurality of attached positions.

Modified Example 2

In the above, at the step S5, positions of the transmitting oscillator 13 and the receiving oscillator 15 are changed in the direction (the left-to-right direction in FIG. 3) in which the transmitting oscillator 13 and the receiving oscillator 15 face each other. However, the present invention is not limited to this. In other words, positions of the transmitting oscillator 13 and the receiving oscillator 15 may be changed in a direction (e.g., the direction perpendicular to the paper sheet surface of FIG. 3) that intersects with the direction in which the transmitting oscillator 13 and the receiving oscillator 15 face each other. In this case, at the step S8, a position of the defect 1*a* in the direction perpendicular to the paper sheet surface of FIG. 3, and a distance from this position to the defect 1*a* can be acquired.

Modified Example 3

In the above, at the step S5, positions of the transmitting oscillator 13 and the receiving oscillator 15 attached to the inspecting target object 1 are changed. However, the present invention is not limited to this. In other words, a plurality of the ultrasonic transmitter 3 and a plurality of the ultrasonic receivers 5 may be installed at attached positions different from each other in the inspecting target object 1. These attached positions are arranged on one straight line. In this case, a pair of the ultrasonic transmitter 3 (transmitting oscillator 13) and the ultrasonic receiver 5 (receiving oscillator 15) are used to perform the step S2. At the step S5, a different pair of the ultrasonic transmitter 3 (transmitting oscillator 13) and the ultrasonic receiver 5 (receiving oscillator 15) are selected, and this different pair of the ultrasonic transmitter 3 and the ultrasonic receiver 5 are used to perform the next step S2. A distance between the ultrasonic transmitter 3 (transmitting oscillator 13) and the ultrasonic receiver 5 (receiving oscillator 15) used in the step S2 is the same for plural times (set number of times) of step S2. In this case, the waveform generating unit 9 and the amplifying unit 11 may be shared with a plurality of the ultrasonic transmitters 3, or may be provided for each ultrasonic transmitter 3. Similarly, the amplifying unit 17 and the waveform recording unit 19 may be shared with a plurality of the ultrasonic receivers 5, or may be provided for each ultrasonic receiver 5.

Modified Example 4

In a case where a position of the defect 1*a* in the inspecting target object 1 is known for a direction along the surface of the inspecting target object 1, a depth of the defect 1*a* is acquired as follows. The above-described steps S4, S5, and S8 are omitted, and a depth of the defect 1*a* is acquired on the basis of a propagation time length acquired at the step S7, and an attached position of the ultrasonic transmitter 3 and the ultrasonic receiver 5.

REFERENCE SIGNS LIST

1 Inspecting target object
1*a* Defect
3 Ultrasonic transmitter
5 Ultrasonic receiver
7 Data processing device
9 Waveform generating unit
10 Ultrasonic inspecting device
11 Amplifying unit
13 Transmitting oscillator
15 Receiving oscillator
17 Amplifying unit
19 Waveform recording unit
21 Pulse compressing unit
23 Propagation time specifying unit
25 Aperture synthesis unit
27 Decomposing unit
29 Time axis adjusting unit
31 Adding unit
33 Ultrasonic transmitter
35 Ultrasonic receiver

The invention claimed is:

1. An ultrasonic inspecting device for making a frequency-modulated ultrasonic wave propagate in an inspecting target object, and acquiring a position of a defect in the inspecting target object on the basis of the frequency-modulated ultrasonic wave reflected by the defect in the inspecting target object, the ultrasonic inspecting device comprising:
    an ultrasonic transmitter attached to the inspecting target object, and causing a frequency-modulated ultrasonic wave propagating in the inspecting target object to be generated;
    an ultrasonic receiver receiving a reflected wave of the frequency-modulated ultrasonic wave that has propagated in the inspecting target object;
    a data processing device acquiring position specifying data for specifying the position of the defect in the inspecting target object, on the basis of received data of the reflected wave received by the ultrasonic receiver, wherein the received data represents an amplitude of the reflected wave at each time point;
    wherein the frequency-modulated ultrasonic wave has a frequency modulated waveform, all frequency components of which are deviated from a resonance frequency of the ultrasonic transmitter and the ultrasonic receiver, and
    the data processing device includes a pulse compressing unit performing pulse compression on the received data, and acquires the position specifying data on the basis of the pulse-compressed received data.

2. The ultrasonic inspecting device according to claim 1, wherein the ultrasonic transmitter generates the frequency-modulated ultrasonic wave for a set time period, and
    an amplitude of the frequency-modulated ultrasonic wave gradually increases from a start time point of the set time period to a first halfway time point, is kept constant from the first halfway time point to a second halfway time point, and gradually decreases from the second halfway time point to an end time point of the set time period.

3. The ultrasonic inspecting device according to claim 1, wherein attached positions of the ultrasonic transmitter and the ultrasonic receiver to the inspecting target object are changed, or a plurality of ultrasonic transmitters and a plurality of ultrasonic receivers are installed at attached positions different from each other,
at each of the attached positions, the ultrasonic transmitter makes the frequency-modulated ultrasonic wave propagate in the inspecting target object, and the ultrasonic receiver receives the reflected wave of the frequency-modulated ultrasonic wave,
the ultrasonic inspecting device includes a waveform recording unit that records the received data acquired for each of the attached positions, and
the data processing device comprises:
a propagation time specifying unit acquiring, as the position specifying data, a propagation time length from a time point when the ultrasonic transmitter generates the frequency-modulated ultrasonic wave to a time point when the ultrasonic receiver receives the reflected wave of the frequency-modulated ultrasonic wave, on the basis of the received data for each of the attached positions; and
an aperture synthesis unit performing aperture synthesis on a plurality of propagation time lengths acquired respectively for a plurality of the attached positions to acquire the position of the defect in the inspecting target object.

4. The ultrasonic inspecting device according to claim 2, wherein attached positions of the ultrasonic transmitter and the ultrasonic receiver to the inspecting target object are changed, or a plurality of ultrasonic transmitters and a plurality of ultrasonic receivers are installed at attached positions different from each other,
at each of the attached positions, the ultrasonic transmitter makes the frequency-modulated ultrasonic wave propagate in the inspecting target object, and the ultrasonic receiver receives the reflected wave of the frequency-modulated ultrasonic wave,
the ultrasonic inspecting device includes a waveform recording unit that records the received data acquired for each of the attached positions, and
the data processing device comprises:
a propagation time specifying unit acquiring, as the position specifying data, a propagation time length from a time point when the ultrasonic transmitter generates the frequency-modulated ultrasonic wave to a time point when the ultrasonic receiver receives the reflected wave of the frequency-modulated ultrasonic wave, on the basis of the received data for each of the attached positions; and
an aperture synthesis unit performing aperture synthesis on a plurality of propagation time lengths acquired respectively for a plurality of the attached positions to acquire the position of the defect in the inspecting target object.

5. An ultrasonic inspecting method for making a frequency-modulated ultrasonic wave propagate in an inspecting target object, and acquiring a position of a defect in the inspecting target object on the basis of the frequency-modulated ultrasonic wave reflected by the defect in the inspecting target object, the ultrasonic inspecting method comprising:
(A) attaching an ultrasonic transmitter and an ultrasonic receiver to the inspecting target object;
(B) by the ultrasonic transmitter, generating the frequency-modulated ultrasonic wave that propagates in the inspecting target object;
(C) by the ultrasonic receiver, receiving a reflected wave of the frequency-modulated ultrasonic wave that has propagated in the inspecting target object by the step (B); and
(D) acquiring position specifying data for specifying the position of the defect in the inspecting target object, on the basis of received data of the reflected wave received by the ultrasonic receiver, wherein the received data represents an amplitude of the reflected wave at each time point;
wherein the frequency-modulated ultrasonic wave generated by the step (B) has a waveform, all frequency components of which are deviated from a resonance frequency of the ultrasonic transmitter and the ultrasonic receiver, and
at the step (D), pulse compression is performed on the received data, and on the basis of the pulse-compressed received data, the position specifying data is acquired.

* * * * *